United States Patent [19]

Nakane et al.

[11] Patent Number: 5,935,832
[45] Date of Patent: Aug. 10, 1999

[54] FARNESYL DIPHOSPHATE SYNTHASE

[75] Inventors: Hiroyuki Nakane; Chikara Ohto, both of Toyota; Shinichi Ohnuma, Sendai; Kazutake Hirooka, Sendai; Tokuzo Nishino, Sendai, all of Japan

[73] Assignee: Toyota Jidosha Kabushiki Kaisha, Toyota, Japan

[21] Appl. No.: 08/898,560

[22] Filed: Jul. 22, 1997

[30] Foreign Application Priority Data

Jul. 24, 1996 [JP] Japan ..................................... 8-213211

[51] Int. Cl.⁶ ............................... C12N 9/10; C12N 1/20; C12N 15/00; C07H 21/04
[52] U.S. Cl. ................. 435/193; 435/252.3; 435/254.11; 435/325; 435/320.1; 435/410; 536/23.2; 935/22
[58] Field of Search ................................ 435/193, 320.1, 435/252.3, 254.11, 325, 410; 536/23.2; 935/22

[56] References Cited

FOREIGN PATENT DOCUMENTS

| | | |
|---|---|---|
| 0 537 553 A2 | 4/1993 | European Pat. Off. . |
| 0 674 000 A2 | 9/1995 | European Pat. Off. . |
| 0 699 761 A2 | 3/1996 | European Pat. Off. . |
| 0 733 709 A2 | 9/1996 | European Pat. Off. . |
| 409065878 | 3/1997 | Japan . |

OTHER PUBLICATIONS

Math, et al., *Proc. Natl. Acad. Sci. USA*, vol. 89, Aug. 1992, pp. 6761–6764.
Ohnuma, et al., *J. Biol. Chem.*, 269:20, May 20 1994, pp. 14792–14797.
Koyama and Ogura, Mechanisms of Isoprenoid Chain Elongation Systems: Cloning and Analysis of Prenyltransferase Genes of *Bacillus stearothermophilus*, English language version of p. 174 of proceedings of the 36th Meeting for Natural Organic Compounds, Hiroshima–shi, Japan, Oct. 27–29, 1994, pp. 167–173.
Koyama, et al., *J. Biochem.*, 113:3, pp. 355–363, 1993.
Chen, et al., *J. Biochem.*, 268:15, pp. 11002–11007, 1993.
Chen, et al., *Arch. Biochem. Biophys.*, 314:2, pp. 399–404, Nov. 1 1994.
Chen, et al., *Protein Science*, vol. 3, pp. 600–607, 1994.
Anderson, et al., *J. Biol. Chem.*, vol. 264, pp. 19176–19184, Nov. 15 1989.
Jeong, et al., *J. DNA Sequencing & Mapping*, vol. 4, pp. 59–67, 1993.
Koike–Takeshita, et al., *J. Biol. Chem.*, 270:31, pp. 18396–18400, Aug. 4, 1995.
Fujisaki, et al., *J. Biochem*, 108:6, pp. 995–1000, 1990.
Ashby, et al., *J. Biol. Chem.*, 265:22, pp. 13157–13164, Aug. 5, 1990.
Teruya, et al., *Mol. Cell. Biol.*, 10:5, pp. 2315–2326, May 1990.
Sheares, et al. *Biochemistry*, 28:20, pp. 8129–8135, 1989.
Wilkin, et al., *J. Biol. Chem.*, 265:8, pp. 4607–4614, Mar. 15, 1990.
Armstrong, et a., *Proc. Natl. Acad. Sci. USA*, vol. 87, pp. 9975–9979, Dec. 1990.
Scolnik, et al., *Plant Physiol.*, vol. 104, pp. 1469–1470, 1994.
Aitken, et al., *Plant Physiol.*, vol. 108, pp. 837–838, 1995.
Badillo, et al., *Plant Mol. Biol.*, vol. 27, pp. 425–428, 1995.
*Plant Physiol.*, 108:3, p. 1343, 1995.
Lang, et al., *J. Bacteriol.*, 177:8, pp. 2064–2073, Apr. 1995.
Armstrong, et al., *Mol. Gen. Genet.*, vol. 216, pp. 254–268, 1989.
EMBL release 45, Dec. 1995 (14 pages).
Carattoli, et al., *J. Biol. Chem.*, 266:9, pp. 5854–5859, Mar. 25, 1991.
Koyama, *Can. J. Chem.*, vol. 72, pp. 75–79, 1994.
Ohnuma, et al., *J. Biol. Chem.*, 271:17, pp. 10087–10095, Apr. 26, 1996.
Koyama, et al., *Biochemistry*, 33:42, pp. 12644–12648, 1994.
Ohnuma, et al., *J. Biol. chem.*, 271:31, pp. 18831–18837, Aug. 2, 1996.
Tarshis, et al., *Biochemistry*,33:36, pp. 10871–10877, 1994.
Koyama, et al., *Biochemistry*, 35:29, pp. 9533–9538, 1996.

*Primary Examiner*—Robert A. Wax
*Assistant Examiner*—Einar Stole
*Attorney, Agent, or Firm*—Kenyon & Kenyon

[57] ABSTRACT

A mutant prenyl diphosphate synthase capable of synthesizing prenyl diphosphates, shorter than those synthesized by the original enzyme, by modifying the amino acid sequence in and upstream of the aspartic acid-rich domain DDXX(XX)D (X denotes any amino acid, and XX in the parentheses may not be present) present in region II of the prenyl diphosphate synthase.

16 Claims, 3 Drawing Sheets

Fig.1

|  | REGION I |  | REGION II |  | REGION III |
|---|---|---|---|---|---|
| ATGERPYRS | 116 GGKRVR | 147 | EMIHTMSLIHDDLPCMDNDDLRRG | 238 | GQVVD |
| LA15778.p | 110 ....... | 141 | ........................ | 230 | ..... |
| CAGERDIS. | 118 ....... | 149 | ........................ | 238 | ..A.. |
| ATGGPSRP. | 88 .P..AP | 119 | ..V.AA..........D.PV.... | 211 | ..Y.. |
| GGPS.pep | 43 ....L. | 74 | .VL.FT.V......I..Q.NI... | 160 | ..A.. |
| SPCRT.pep | 64 .A_.I. | 95 | .L..CA..V......F.DAEI... | 185 | ..GWE |
| RCPHSYNG. | 192 .A_.I. | 223 | .LM.CA..V........A.I.... | 313 | ..AWE |
| EHCRTS.pe | 54 ...I. | 86 | .LT..A..ML...M...AE..... | 175 | ..FR. |
| MXCRTNODA | 104 ..L. | 136 | .LL..FL.........VA.QAE.. | 199 | ..YL. |
| NCAL3.pep | 197 .DI. | 226 | _.L..A..LV......VE..SV.. | 260 | ..GM. |

|  | REGION IV |  | REGION V |
|---|---|---|---|
| ATGERPYRS | 265 KT | 293 | GLLFQVVDDIL_DVTKSSK_ELGKTAGKDLIADK |
| LA15778.p | 255 .. | 283 | .M.............V........V... |
| CAGERDIS. | 263 .. | 291 | ........................VV.. |
| ATGGPSRP. | 230 .F | 256 | .M.Y........TE.KK..YDGGAE.GMMEMAEEL. |
| GGPS.pep | 185 .. | 211 | .IA...I......GLTADEKE.....PVFS.IREG. |
| SPCRT.pep | 203 .. | 227 | .EA...A..LR..ALCDAE_T....P..Q.E.HAR. |
| RCPHSYNG. | 331 .. | 355 | .SA..IA..LK..ALM.AE_AM...P..Q.IANER. |
| EHCRTS.pe | 199 .. | 225 | .QA..LL..LRD.HPET.......DRN..A_.G... |
| MXCRTNODA | 226 .. | 247 | ..AY.LR..L.GLFGD.NV___A..A.DG.FLQG.. |
| NCAL3.pep | 286 .. | 272 | ..I...IA..YHNLWNREYT___AN.GMCE..TEG. |

Fig. 3

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 330 amino acids
      (B) TYPE: amino acid
      (D) TOPOLOGY: linear    (ii) MOLECULE TYPE: protein    (vi) ORIGINAL SOURCE:
      (A) ORGANISM: Sulfolobus acidocaldarius
      (B) STRAIN: ATCC 33909

(ix) FEATURE:
      (A) NAME/KEY: Asp-rich domain
      (B) LOCATION: 82-86

(xi) SEQUENCE DESCRIPTION: SEQ ID NO:1:

```
Met Ser Tyr Phe Asp Asn Tyr Phe Asn Glu Ile Val Asn Ser Val Asn
                 5                  10                  15

Asp Ile Ile Lys Ser Tyr Ile Ser Gly Asp Val Pro Lys Leu Tyr Glu
             20                  25                  30

Ala Ser Tyr His Leu Phe Thr Ser Gly Gly Lys Arg Leu Arg Pro Leu
         35                  40                  45

Ile Leu Thr Ile Ser Ser Asp Leu Phe Gly Gly Gln Arg Glu Arg Ala
     50                  55                  60

Tyr Tyr Ala Gly Ala Ala Ile Glu Val Leu His Thr Phe Thr Leu Val
 65                  70                  75                  80

His Asp Asp Ile Met Asp Gln Asp Asn Ile Arg Arg Gly Leu Pro Thr
                 85                  90                  95

Val His Val Lys Tyr Gly Leu Pro Leu Ala Ile Leu Ala Gly Asp Leu
            100                 105                 110

Leu His Ala Lys Ala Phe Gln Leu Leu Thr Gln Ala Leu Arg Gly Leu
        115                 120                 125

Pro Ser Glu Thr Ile Ile Lys Ala Phe Asp Ile Phe Thr Arg Ser Ile
    130                 135                 140

Ile Ile Ile Ser Glu Gly Gln Ala Val Asp Met Glu Phe Glu Asp Arg
```

```
                145                 150                 155                 160
Ile Asp Ile Lys Glu Gln Glu Tyr Leu Asp Met Ile Ser Arg Lys Thr
                    165                 170                 175

Ala Ala Leu Phe Ser Ala Ser Ser Ile Gly Ala Leu Ile Ala Gly
            180                 185                 190

Ala Asn Asp Asn Asp Val Arg Leu Met Ser Asp Phe Gly Thr Asn Leu
                195                 200                 205

Gly Ile Ala Phe Gln Ile Val Asp Asp Ile Leu Gly Leu Thr Ala Asp
            210                 215                 220

Glu Lys Glu Leu Gly Lys Pro Val Phe Ser Asp Ile Arg Glu Gly Lys
225                 230                 235                 240

Lys Thr Ile Leu Val Ile Lys Thr Leu Glu Leu Cys Lys Glu Asp Glu
                245                 250                 255

Lys Lys Ile Val Leu Lys Ala Leu Gly Asn Lys Ser Ala Ser Lys Glu
            260                 265                 270

Glu Leu Met Ser Ser Ala Asp Ile Ile Lys Lys Tyr Ser Leu Asp Tyr
                275                 280                 285

Ala Tyr Asn Leu Ala Glu Lys Tyr Tyr Lys Asn Ala Ile Asp Ser Leu
            290                 295                 300

Asn Gln Val Ser Ser Lys Ser Asp Ile Pro Gly Lys Ala Leu Lys Tyr
305                 310                 315                 320

Leu Ala Glu Phe Thr Ile Arg Arg Lys
                325                 330
```

(2) INFORMATION FOR SEQ ID NO:2:

(i) SEQUENCE CHARACTERISTICS:
        (A) LENGTH: 993 base pairs
        (B) TYPE: nucleic acid
        (C) STRANDEDNESS: double
        (D) TOPOLOGY: linear     (ii) MOLECULE TYPE: genomic DNA     (vi) ORIGINAL SOURCE:
        (A) ORGANISM: Sulfolobus acidocaldarius
        (B) STRAIN: ATCC 33909

(ix) FEATURE:
        (A) NAME/KEY: Asp-rich domain coding
        (B) LOCATION: 246-258

(xi) SEQUENCE DESCRIPTION: SEQ ID NO:2:

```
ATGAGTTACT TTGACAACTA TTTTAATGAG ATTGTTAATT CTGTAAACGA CATTATTAAG     60

AGCTATATAT CTGGAGATGT TCCTAAACTA TATGAAGCCT CATATCATTT GTTTACATCT    120

GGAGGTAAGA GGTTAAGACC ATTAATCTTA ACTATATCAT CAGATTTATT CGGAGGACAG    180

AGAGAAAGAG CTTATTATGC AGGTGCAGCT ATTGAAGTTC TTCATACTTT TACGCTTGTG    240

CATGATGATA TTATGGATCA AGATAATATC AGAAGAGGGT TACCCACAGT CCACGTGAAA    300

TACGGCTTAC CCTTAGCAAT ATTAGCTGGG GATTTACTAC ATGCAAAGGC TTTTCAGCTC    360

TTAACCCAGG CTCTTAGAGG TTTGCCAAGT GAAACCATAA TTAAGGCTTT CGATATTTTC    420

ACTCGTTCAA TAATAATTAT ATCCGAAGGA CAGGCAGTAG ATATGGAATT TGAGGACAGA    480

ATTGATATAA AGGAGCAGGA ATACCTTGAC ATGATCTCAC GTAAGACAGC TGCATTATTC    540

TCGGCATCCT CAAGTATAGG CGCACTTATT GCTGGTGCTA ATGATAATGA TGTAAGACTG    600

ATGTCTGATT TCGGTACGAA TCTAGGTATT GCATTTCAGA TTGTTGACGA TATCTTAGGT    660

CTAACAGCAG ACGAAAAGGA ACTTGGAAAG CCTGTTTTTA GTGATATTAG GGAGGGTAAA    720
```

```
AAGACTATAC TTGTAATAAA AACACTGGAG CTTTGTAAAG AGGACGAGAA GAAGATTGTC      780

CTAAAGGCGT TAGGTAATAA GTCAGCCTCA AAAGAAGAAT TAATGAGCTC AGCAGATATA      840

ATTAAGAAAT ACTCTTTAGA TTATGCATAC AATTTAGCAG AGAAATATTA TAAAAATGCT      900

ATAGACTCTT TAAATCAAGT CTCCTCTAAG AGTGATATAC CTGGAAAGGC TTTAAAATAT      960

CTAGCTGAAT TTACGATAAG AAGGAGAAAA TAA                                   993
```

(2) INFORMATION FOR SEQ ID NO:3:

(i) SEQUENCE CHARACTERISTICS:
        (A) LENGTH:37
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:3:

```
CATACTTTTT TCCTTGTGGC TGATGATATC ATGGATC                               37
```

(2) INFORMATION FOR SEQ ID NO:4:

(i) SEQUENCE CHARACTERISTICS:
        (A) LENGTH:37
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:4:

```
CATACTTTTT TCCTTGTGCT TGATGATATC ATGGATC                               37
```

(2) INFORMATION FOR SEQ ID NO:5:

(i) SEQUENCE CHARACTERISTICS:
        (A) LENGTH:37
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:5:

```
CATACTTATT TCCTTGTGCT TGATGATATC ATGGATC                               37
```

(2) INFORMATION FOR SEQ ID NO:6:

(i) SEQUENCE CHARACTERISTICS:
        (A) LENGTH:37
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:6:

```
CATACTTATT TCCTTGTGGC TGATGATATC ATGGATC                               37
```

(2) INFORMATION FOR SEQ ID NO:7:

(i) SEQUENCE CHARACTERISTICS:
        (A) LENGTH: 36
        (B) TYPE: nucleic acid
        (C) STRANDEDNESS: single
        (D) TOPOLOGY: linear     (ii) MOLECULE TYPE: cDNA (xi) SEQUENCE DESCRIPTION: SEQ ID NO:7:

GTTCTTCATA CTTATTCGCT TATTCATGAT AGTATT                36

(2) INFORMATION FOR SEQ ID NO:8:

(i) SEQUENCE CHARACTERISTICS:
        (A) LENGTH: 33
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:8:

ATTCATGATG ATCTTCCATC GATGGATCAA GAT                  33

(2) INFORMATION FOR SEQ ID NO:9:

(i) SEQUENCE CHARACTERISTICS:
        (A) LENGTH: 27
        (B) TYPE: nucleic acid
        (C) STRANDEDNESS: single
        (D) TOPOLOGY: linear     (ii) MOLECULE TYPE:  cDNA     (xi) SEQUENCE DESCRIPTION: SEQ ID NO:9:

TTTTTCCTTG TGGCTGATGA TATCATG                         27

(2) INFORMATION FOR SEQ ID NO:10:

(i) SEQUENCE CHARACTERISTICS:
        (A) LENGTH: 27
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:10:

TTTTTCCTTG TGCTTGATGA TATCATG                         27

(2) INFORMATION FOR SEQ ID NO:11:

(i) SEQUENCE CHARACTERISTICS:
        (A) LENGTH: 27
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:11:

TATTTCCTTG TGCTTGATGA TATCATG                         27

(2) INFORMATION FOR SEQ ID NO:12:

(i) SEQUENCE CHARACTERISTICS:
        (A) LENGTH: 27
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:12:

TATTTCCTTG TGGCTGATGA TATCATG                         27

(2) INFORMATION FOR SEQ ID NO:13:

(i) SEQUENCE CHARACTERISTICS:
        (A) LENGTH: 33
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:13:

TATTCGCTTA TTCATGATGA TCTTCCATCG ATG          33

(2) INFORMATION FOR SEQ ID NO:14:

(i) SEQUENCE CHARACTERISTICS:
        (A) LENGTH: 27
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:14:

TTTACGCTTG TGCATGATGA TATTATG          27

FARNESYL DIPHOSPHATE SYNTHASE

BACKGROUND OF INVENTION

1. Field of Invention

The present invention relates to a novel mutant enzyme which synthesizes linear prenyl diphosphates that are precursors of compounds, important for organisms, such as steroids, ubiquinones, dolichols, carotenoids, prenylated proteins, animal hormones, plant hormones, and the like; a genetic system encoding said enzyme; and a method for producing and using said enzyme.

2. Related Art

Of the substances having important functions in organisms, many are biosynthesized using isoprene (2-methyl-1,3-butadiene) as a constituent units. These compounds are also called isoprenoids, terpenoids, or terpenes, and are classified depending on the number of carbon atoms into hemiterpenes (C5), monoterpenes (C10), sesquiterpenes (C15), diterpenes (C20), sesterterpenes (C25), triterpenes (C30), tetraterpenes (C40), and the like. The actual biosynthesis starts with the mevalonate pathway through which mevalonic acid-5-diphosphate is synthesized, followed by the synthesis of isopentenyl diphosphate (IPP) which is an active isoprene unit.

The identity of the isoprene unit that was proposed as a precursor was found to be isopentenyl diphosphate, the so-called active isoprene unit. Dimethylallyl diphosphate (DMAPP), an isomer of isopentenyl diphosphate, being used as a substrate in the synthesis of isopentenyl adenine which is known as a cytokinin, one of the plant hormones, it is also known to undergo a condensation reaction with isopentenyl diphosphate to synthesize chain-form active isoprenoids such as geranyl diphosphate (GPP), neryl diphosphate, farnesyl diphosphate (FPP), geranylgeranyl diphosphate (GGPP), geranylfarnesyl diphosphate (GFPP), hexaprenyl diphosphate (HexPP), heptaprenyl diphosphate (HepPP), and the like.

There are Z type and E type condensation reactions. Geranyl diphosphate is a product of E type condensation and neryl diphosphate is of Z type condensation. Although, the all-E type is considered to be the active form in farnesyl diphosphate and geranylgeranyl diphosphate, the Z type condensation reaction leads to the synthesis of natural rubber, dolichols, bactoprenols (undecaprenols), and plants various polyprenols found in. They are believed to undergo the condensation reaction using the phosphate ester bond energy of the pyrophosphate and the carbon backbone present in the molecule and to produce pyrophosphate as the byproduct of the reaction.

Farnesyl diphosphate or geranylgeranyl diphosphate serve as a reaction substrate leading to the synthesis of prenylated proteins (from farnesyl diphosphate or geranylgeranyl diphosphate) represented by G proteins that are important in the mechanism of signal transducer in the cell; cell membrane lipids (from geranylgeranyl diphosphate) of archaea; squalene (from farnesyl diphosphate) which is a precursor of steroids; and phytoene (from geranylgeranyl diphosphate) which is a precursor of carotenoids. Prenyl diphosphates from hexaprenyl diphosphate and heptaprenyl diphosphate having six and seven isoprene units, respectively, to prenyl diphosphates having ten isoprene units serve as the precursors of the synthesis of ubiquinone and menaquinone (vitamin K2) that work in the electron transport system.

Furthermore, via the biosynthesis of these active-form isoprenoids, a vast number of kinds of compounds that are vital to life have been synthesized. Just to mention a few, there are cytokinins that are plant hormones and isopentenyl adenosine-modified tRNA that use hemiterpenes as their precursor of synthesis, geraniols and that isomer nerol belonging to monoterpens are the main components of rose oil perfume and a camphor tree extract, camphor, which is an insecticide. Sesquihormones include juvenile hormones of insects, diterpenes include a plant hormone gibberellin, trail pheromones of insects, and retinols and retinals that function as the visual pigment precursors, binding components of the purple membrane proteins of highly halophilic archaea, and vitamin A.

Furthermore, using squalene, a triterpene, a wide variety of steroid compounds have been synthesized, including, for example, animal sex hormones, vitamin D, ecdysone which is an ecdysis hormone of insects, a plant hormone brassinolide, constitution of the plasma membrane etc. Various carotenoids of tetraterpenes that are precursors of various pigments of organisms and vitamin A are also important compounds derived from active isoprenoids. Compounds such as chlorophyll, pheophytin, tocopherol (vitamin E), and phylloquinone (vitamin K1) are also derived from tetraterpenes.

The active isoprenoid synthases that sequentially condense isopentenyl diphosphates with such allylic substrates as dimethylallyl diphosphate, geranyl diphosphate, farnesyl diphosphate, geranylgeranyl diphosphate, geranylfarnesyl diphosphate, etc. are called the prenyl diphosphate synthases, and are also called, based on the name of the compound having the maximum chain length of the major reaction products, for example farnesyl diphosphate synthase (FPP synthase), geranylgeranyl diphosphate (GGPP synthase), and the like. There are reports on purification, activity measurement, genetic cloning, and sequencing of the DNA encoding enzymes such as farnesyl diphosphate synthase, geranylgeranyl diphosphate synthase, hexaprenyl diphosphate synthase, heptaprenyl diphosphate synthase, octaprenyl diphosphate synthase, nonaprenyl diphosphate synthase (solanesyl diphosphate synthase), undecaprenyl diphosphate synthase, and the like from bacteria, archaea, fungi, plants, and animals.

These active isoprenoid synthases constituting the basis of chemical synthesis of a great variety of compounds that are important both in the industry and in the academic field of life sciences have had few practical uses in the industrial application due to their unstable nature and low specific activities. However, with the isolation of thermostable prenyl diphosphate synthases from thermophilic bacteria and archaea and the genes encoding these enzymes, their availability as the enzyme has increased.

With regard to farnesyl diphosphate synthase, a gene was isolated from *Bacillus stearothermophilus*, a medium thermophile, and an enzyme having a medium thermal stability was prepared using *Escherichia coli* as host cell [T. Koyama et al. (1993) J. Biochem., 113: 355–363; Japanese Unexamined Patent Publication No. 5(1993)-219961]. With regard to geranylgeranyl diphosphate synthase, a gene was isolated from high thermophiles such as *Sulfolobus acidocaldarius* and *Thermus thermophilus* [S. -i. Ohnuma et al., (1994) J. Biol. Chem., 269: 14792–14797; Japanese Unexamined Patent Publication No. 7(1995)-308193, and; Japanese Unexamined Patent Publication No. 7(1995)-294956], and enzymes having a high thermal stability were prepared.

Furthermore, with regard to the prenyl diphosphate synthase having the functions of both of the farnesyl diphosphate synthase and the geranylgeranyl diphosphate synthase, the enzyme and the gene encoding it have been isolated from highly thermophile *Methanobacterium thermoautotrophicum* [A. Chen and D. Poulter (1993) J. Biol. Chem., 268: 11002–11007; A. Chen and D. Poulter (1994) ARCHIVES OF BIOCHEMSTRY AND BIOPHYTSICS 314], and the thermostable nature of the enzyme has been demonstrated.

However, in the synthesis of farnesyl diphosphate/geranylgeranyl diphosphate derived from *Methanobacterium thermoautotrophicum,* there are no reports on the data of thin layer chromatography analysis etc. that can specify the chain length of the reaction products in connection with the assay of the enzymatic activity; the chain length has been estimated by measuring geranyl diphosphate as the allylic substrate. Since geranyl diphosphate can also serve as a substrate of geranylgeranyl diphosphate synthase, it is unlikely that the measured activity includes that of the farnesyl diphosphate synthase alone.

Moreover, the presence of farnesyl diphosphate synthase has not been confirmed in archaea that are expected to have enzymes having higher thermo stability, higher salt-stability and lower-pH-stability.

As mentioned above, the use of the farnesyl diphosphate synthase derived from *Bacillus stearothermophilus* resolved part of the problem of the enzyme being unstable and difficult to handle. But, an enzyme having a higher thermal stability would be more stable and more amenable to industrial application.

Moreover, some prenyl diphosphate synthases having a longer chain length use farnesyl diphosphate as a substrate. When such a long-chain prenyl diphosphate synthase is used simultaneously with a farnesyl diphosphate synthase for the purpose of providing the substrate of the former enzyme, the latter enzyme must have stability which is equal to or higher than that of the long-chain prenyl diphosphate synthase. When industrial production of farnesyl diphosphate is contemplated, the enzyme must be immobilized or recovered for recycling. When it is regenerated, the enzyme itself to be more stable, must have higher thermo stability, higher salt stability, and higher stability in a wider range of pH.

It has been found out that of the two aspartic acid-rich domains that have been proposed based on the amino acid sequence of the prenyl diphosphate synthase, the amino acid residue located at the fifth position in the N-terminal direction from the conserved sequence I (DDXX(XX)D) (wherein X denotes any amino acid, and the two X's in the parentheses may not be present) of the aspartic acid-rich domain in the amino-terminal side is responsible for controlling the chain length of the reaction product. Hence, a method has been invented that controls the reaction product for the purpose of lengthening the chain length of the reaction product [Japanese patent application No. 8-191635 filed on Jul. 3, 1996 under the title of "A Mutant Prenyl Diphosphate Synthase"]. The enzyme produced using the method enables production of reaction products that have several chain lengths. However, methods have not been not known that induce mutation of geranylgeranyl diphosphate synthase to control the reaction products to be in the short chain-length side in order to produce farnesyl diphosphate.

SUMMARY OF INVENTION

It is an object of the invention to establish a process for producing farnesyl diphosphate synthases by modifying amino acid sequences of prenyl diphosphate enzymes. A new enzyme that is more stable or that has a high specific activity more adaptable to industrial application would make it possible to obtain immediately a mutant prenyl diphosphate synthase or the gene thereof that produces farnesyl diphosphate and that retains the property owned by the the prenyl diphosphate synthase prior to mutation.

From the information on the nucleotide sequence of the gene of the geranylgeranyl diphosphate synthase of the mutant *Sulfolobus acidocaldarius* (*S. acidocaldarius*), it was clarified that out of the two Aspartic acid-rich domains that have been proposed based on the analysis of the amino acid sequence of prenyl diphosphate synthases, the amino acid residues within the aspartic acid-rich domain conserved sequence I (DDXX(XX)D) at the amino terminal side or the five amino acid residues to the N-terminal side from the amino terminal of said conserved sequence I are involved in the control of chain length of the reaction products.

Thus, the present invention provides a mutant prenyl diphosphate synthase having a modified amino acid sequence, wherein at least one amino acid residue selected from (a) the amino acid residues in between the amino acid residue located at the fifth position in the N-terminal direction from D of the N-terminal and the amino acid residue located at the first position in the N-terminal direction from D of said N-terminal of the aspartic acid-rich domain DDXX(XX)D (wherein X sequence denotes any amino acid, and the two X's in the parentheses may not be present) present in region II, and (b) the amino acid residue located at the position in the N-terminal direction from D of the C-terminal of said aspartic acid-rich domain has been substituted by another amino acid, and/or additional amino acid(s) have been inserted in between the amino acid residue located at the first position in the N-terminal direction from D of the C-terminal and D of said C-terminal of said aspartic acid-rich domain.

The present invention provides a farnesyl diphosphate-producing mutant prenyl diphosphate synthase which retains the properties that were owned by the native prenyl diphosphate synthase.

The present invention also provides a DNA or an RNA encoding the above enzyme.

The present invention further provides a recombinant vector and more specifically an expression vector comprising the above DNA.

The present invention further provides a host transformed by the above vector.

The present invention further provides a process for producing prenyl diphosphates having not more than 15 carbons comprising the step wherein the above enzyme is brought into contact with a substrate selected from the group consisting of isopentenyl diphosphate, dimethylallyl diphosphate, and geranyl diphosphate.

The present invention further provides a process of production of a mutant enzyme according to any of claims 1 to 8, said method comprising the steps of culturing the above host and of harvesting the expression product from the culture.

BRIEF EXPLANATION OF THE DRAWINGS

FIG. 1 is a graph showing the regions (I) to (V) and the aspartic acid-rich domain I of various prenyl diphosphate synthases. In the figure, the sequence represents the amino acid sequence of geranylgeranyl diphosphate synthase, and ATGERPYRS is the one derived from *Arabidopsis thaliana,* LA15778.p from *Lupinas albus,* CAGERDIS from *Capsicum annuum,* ATGGPSRP from *Arabidopsis thaliana,* GGPS-pep from *Sulfolobus acidocaldarius,* SPCRT.pep from *Rhodobactor sphaeroides*, RCPHSYNG from *Rhodobactor capsulatus*, EHCRTS.pe from *Erwinia herbicola*, MXCRTNODA from *Myxococcus thaliana*, and NCAL3.pep from *Neurospora crassa*. The number indicated on the left of each amino acid sequence represents the site from the N-terminal side of each geranylgeranyl diphosphate synthase at the N-terminal of the amino acid sequence.

GOH is geraniol, FOH is farnesol, GGOH is geranyl geraniol, and GFOH is geranylfarnesol, and these are produced from dephosphorylation of geranyl diphosphate, farnesyl phosphate, geranylgeranyl diphosphate, and geranylfarnesyl diphosphate, respectively. SacGGPS is the geranylgeranyl diphosphate synthase prior to mutation. The others are each mutant enzymes.

DETAILED DESCRIPTION

It has been proposed that there are five conserved regions in the amino acid sequence of a prenyl diphosphate synthase (one subunit in the case of a heterodimer) [A. Chem et al., Protein Science Vol. 3, pp. 600–607, 1994]. It is also known that of the five conserved regions, there is an aspartic acid-rich domain conserved sequence I [DDXX(XX)D] (wherein X denotes any amino acid, and the two X's in the parentheses may not be present) in region II. Although there is also an aspartic acid-rich domain indicated as "DDXXD" in region V, the aspartic acid-rich domain used to specify the modified region of the amino acid sequence of the present invention is the one present in region II, and this domain is termed as the aspartic acid-rich domain I as compared to the aspartic acid-rich domain II present in region V.

As the prenyl diphosphate synthases having the aspartic acid-rich domain as described above, there can be mentioned farnesyl diphosphate synthase, geranylgeranyl diphosphate synthase, hexaprenyl diphosphate synthase, heptaprenyl diphosphate synthase, octaprenyl diphosphate synthase, nonaprenyl diphosphate synthase, undecaprenyl diphosphate synthase, and the like. More specific examples include the farnesyl diphosphate synthase of *Bacillus stearothermophilus*, the farnesyl diphosphate synthase of *Escherichia coli*, the farnesyl diphosphate synthase of *Saccharomyces cerevisiae*, the farnesyl diphosphate synthase of the rat, the farnesyl diphosphate synthase of the human, the geranylgeranyl diphosphate synthase of *Neurospora crassa*, the hexaprenyl diphosphate synthase of *Saccharomyces cerevisiae*, and the like.

Figure 1:
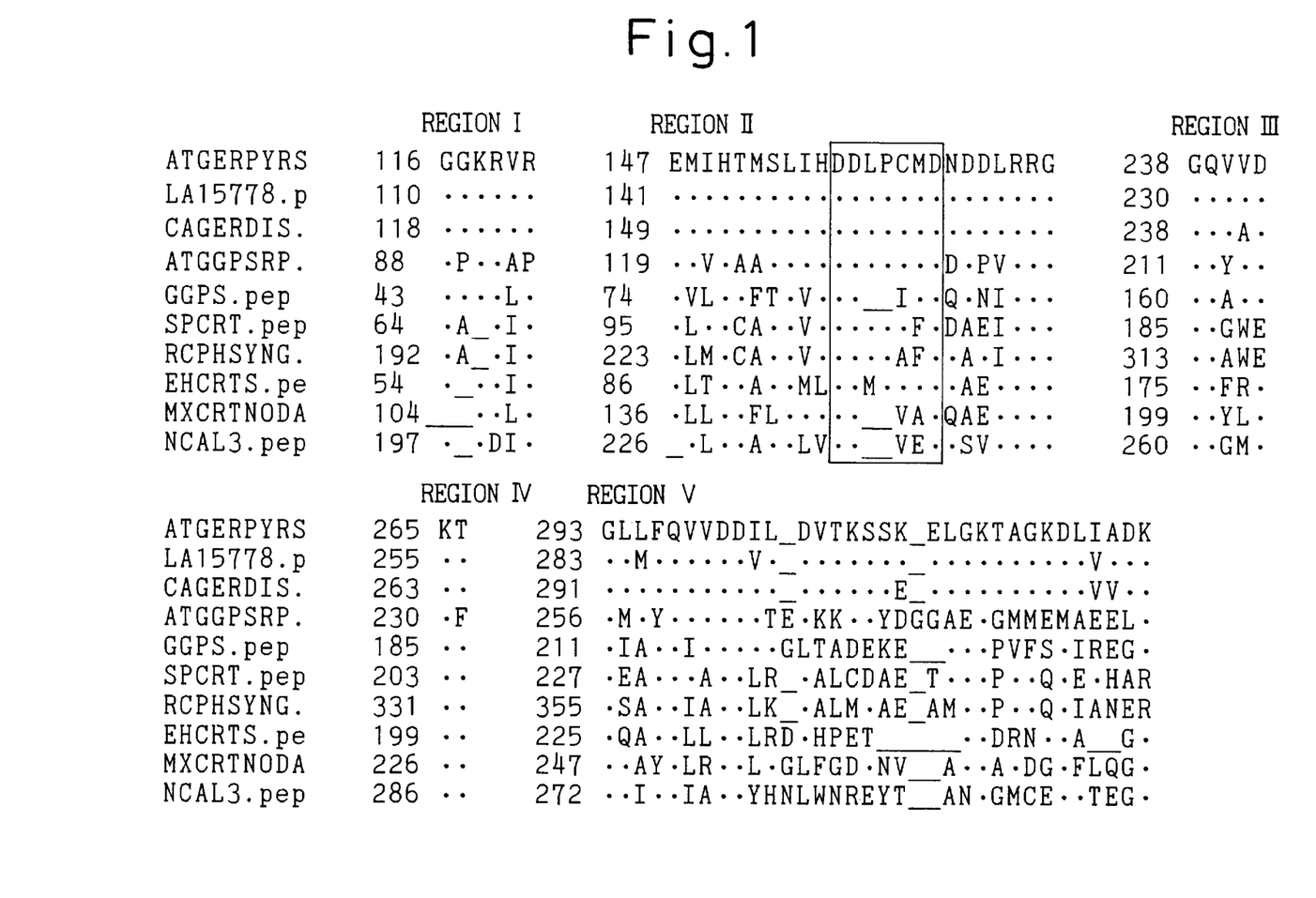

By way of example of some of these, regions I to V and the aspartic acid-rich domain I (in the box) in region II of the amino acid sequence of geranylgeranyl diphosphate synthases are shown in FIG. 1.

The present invention can be applied to any prenyl diphosphate synthase having the aspartic acid-rich domain I.

In accordance with the present invention, in the amino acid sequence of a prenyl diphosphate synthase, at least one amino acid residue selected from (a) the amino acid residues in between the amino acid residue located at the fifth position in the N-terminal direction from D of the N-terminal and the amino acid residue located at the first position in the N-terminal direction from D of said N-terminal of the aspartic acid-rich domain DDXX(XX)D (wherein X denotes any amino acid, and the two X's in the parentheses may not be present) present in region II, and (b) the amino acid residue located at the first position in the N-terminal direction from D of the C-terminal of said aspartic acid-rich domain has been substituted by another amino acid, and/or an additional one or more amino acids have been inserted in between the amino acid residue located at the first position in the N-terminal side from D of the C-terminal and D of said C-terminal of said aspartic acid-rich domain.

The mutant prenyl diphosphate synthase of the present invention can synthesize a farnesyl diphosphate having a shorter chain length than the prenyl diphosphate synthesized by the native prenyl diphosphate synthase.

In accordance with the present invention, by way of example, the gene of the geranylgeranyl diphosphate synthase of a highly thermophilic archaea, *Sulfolobus acidocaldarius*, is used as the starting material. *Sulfolobus acidocaldarius* is available from ATCC as ATCC No. 33909. The method for cloning the gene has been described in detail in Japanese Unexamined Patent Publication No. 7-308193. It has also been disclosed with the accession No. D28748 in the gene information data base such as GenBank. By using the sequence it can be cloned in the conventional method known in the art. An example of the other cloning methods is illustrated in Example 1 herein and its nucleotide sequence is shown as SEQ ID No: 2.

More specifically, the mutant enzyme of the present invention is a mutant prenyl diphosphate synthase characterized in that at least one amino acid selected from phenylalanine in position 77, threonine at position 78, valine at position 80, histidine at position 81, and isoleucine at position 84 has been substituted by another amino acid, and/or amino acid(s) have been inserted in between isoleucine at position 84 and methionine at position 85 in the geranylgeranyl diphosphate synthase having the amino acid sequence as set forth in SEQ ID No: 1.

By way of example, there is provided the amino acid sequences wherein the amino acids have been substituted as shown below:

Mutant enzyme 1: Changes from threonine at position 78 to phenylalanine, and histidine at position 81 to alanine;

Mutant enzyme 2: Changes from threonine at position 78 to phenylalanine, and histidine at position 81 to leucine;

Mutant enzyme 3: Changes from phenylalanine at position 77 to tyrosine, threonine at position 78 to phenylalanine, and histidine at position 81 to leucine;

Mutant enzyme 4: Changes from phenylalanine at position 77 to tyrosine, threonine at position 78 to phenylalanine, and histidine at position 81 to alanine;

Mutant enzyme 5: Changes from phenylalanine at position 77 to tyrosine, threonine at position 78 to serine, valine at position 80 to isoleucine, and isoleucine at position 84 to leucine, and an insertion of proline and serine in between isoleucine at position 84 and methionine at position 85.

In accordance with the present invention, it is indicated that the mutant prenyl diphosphate synthase retains the characteristic properties that were owned by the native prenyl diphosphate synthase. By way of example, the above-mentioned five mutant enzymes show thermo resistance almost equal to that owned by the native geranylgeranyl diphosphate synthase.

It is known that an enzyme can sometimes exhibit its original enzymatic activity even when it has been modified by addition, removal, and/or substitution of one or a few amino acids as compared to the original amino acid sequence. Therefore, the present invention is intended to encompass those enzymes that have been modified by addition, deletion, and/or substitution of one or a few, for example up to five, or up to 10, amino acids as compared to the amino acid sequence as set forth in SEQ ID No: 1 and that can perform its original function.

The present invention also provides the genes encoding various mutant enzymes mentioned above, the vectors containing those genes, specifically expression vectors, and the hosts transformed by said vectors. The gene (DNA) of the present invention can be readily obtained, for example, by introducing mutation into the DNA encoding the original amino acid sequence as set forth in SEQ ID No: 1 using a conventional method such as site-directed mutagenesis, PCR and the like.

Furthermore, once the amino acid sequence of the desired enzyme has been determined, an appropriate nucleotide sequence encoding it can be determined, and the DNA can be chemically synthesized in accordance with a conventional method of DNA synthesis.

The present invention further provides an expression vector comprising DNA such as the one mentioned above, the host transformed by said expression vector, and a method for producing the enzyme or peptide of the present invention using these hosts.

Expression vectors contain an origin of replication, expression regulatory sequences etc., but they may differ depending on hosts used. As the hosts, there are mentioned procaryotes, for example, bacteria such as *Escherichia coli*, organisms of genus Bacillus such as *Bacillus subtilis,* and eukaryotic microorganisms, for example, fungi, for example yeast, for example *Saccharomyces cerevisiae* of genus Saccharomyces and *Pichia pastoris* of genus Pichia, filamentous fungi, for example the genus Asperaillus such as *Asperaillus niger,* animal cells, for example the cultured cells of the silkworm, cultured cells of higher animals, for example CHO cells, and the like. Furthermore, plants may also be used as the host.

As set forth in Examples, in accordance with the present invention, by cultivating the host transformed by the DNA of the present invention, farnesyl diphosphates may be accumulated in the culture broth, which may be harvested to produce their farnesyl diphosphates. Furthermore, in accordance with the invention, farnesyl diphosphates may also be produced by contacting the mutant prenyl diphosphate synthase produced by the method of the invention to the substrate isopentenyl diphosphate and each allyl substrate such as dimethylallyl diphosphate and geranyl diphosphate.

When *Escherichia coli* is used as the host, it is known that the host has the regulatory functions at the stage of transcribing mRNA from DNA and of translating protein from mRNA. As the promoter sequence regulating mRNA synthesis, in addition to the naturally occurring sequences (for example, lac, trp, bla, lpp, $P_L$, $P_R$, ter, T3, T7, etc.), there are known their mutants (for example, lac UV5), and the sequences (such as tac, trc, etc.) in which a naturally occurring promoter is artificially fused, and they can be used for the present invention.

It is known that the distance between the sequence of the ribosome biding site (GGAGG and similar sequences thereof) and the initiation codon ATG is important as the sequence regulating the ability of synthesizing protein from mRNA. It is also well known that a terminator (for example, a vector containing rrn $PT_1$ $T_2$ is commercially available from Pharmacia) that directs transcription termination at the 3'-end affects the efficiency of protein synthesis by a recombinant.

As the vectors that can be used for preparation of the recombinant vectors of the present invention, commercially available vectors are used as they are, or various vectors may be mentioned that are derived depending on the intended use. For example, there can be mentioned pBR322, pBR327, pKK223-3, pKK233-3, pTrc99, and the like having a replicon derived from pMB1; pUC18, pUC19, pUC118, pUC119, pTV118N, pTV119N, pBluescript, pHSG298, pHSG396, and the like that have been altered to enhance copy numbers; and pACYC177, pACYC184, and the like that have a replicon derived from p15A; and, furthermore, plasmids derived from pSC101, ColE1, R1, F factor, and the like.

Furthermore, fusion protein-expressing vectors that enable easier purification such as pGEX-2T, pGEX-3X, pMal-c2 may be used. One example of the gene used as the starting material of the present invention has been described in Japanese Unexamined Patent Publication No. 7-308193.

Furthermore, in addition to plasmids, virus vectors such as λ phage or M13 phage, or transposon may be used for the transformation of genes. With regard to the transformation of the gene into microorganisms other than *Escherichia coli,* gene transformation into organisms of genus Bacillus by pUB110 (commercially available from Sigma) or pHY300PLK (commercially available from Takara Shuzo) is known. These vectors are described in "Molecular Cloning" (J. Sambrook, E. F. Fritsch, and T. Maniatis, Cold Spring Harbor Laboratory Press) and "Cloning Vector" (P. H. Pouwels, B. B. Enger, Valk, and W. J. Brammar, Elsevier), and catalogues of the manufacturers.

Integration of the DNA fragment encoding the prenyl diphosphate synthase and, where needed, the DNA fragment having the function of regulating expression of the gene of said enzyme into these vectors can be performed by a known method using an appropriate restriction enzyme and ligase. Specific examples of the plasmids thus constructed include, for example, pBs-SacGGPS.

As the microorganisms into which genes can be directly introduced using such recombinant vectors include *Escherichia coli* and microorganisms of the genus Bacillus. Such transformation can also be carried out using general method, for example the $CaCl_2$ method and the protoplast method as described in "Molecular Cloning" (J. Sambrook, E. F. Fritsch, and T. Maniatis, Cold Spring Harbor Laboratory Press) and "DNA Cloning" Vol. I to III (D. M. Clover ed., IRL PRESS).

In order to produce the mutant enzyme of the present invention, a host transformed as above is cultured, and then said culture is subjected to any method comprising salting out, precipitation with an organic solvent, gel chromatography, affinity chromatography, hydrophobic chromatography, ion exchange chromatography, and the like to recover and purify said enzyme.

The present invention also provides a process for producing farnesyl diphosphates using the enzyme of the present invention. According to this process, the enzyme of the present invention is reacted with a substrate in a medium, particularly an aqueous medium, and then, as desired, the prenyl diphosphate is harvested from the reaction medium.

As the enzyme, not only a purified enzyme but also a crude enzyme that may be semi-purified to various stages, or a mixture of the cultured broth of a microorganism may be used. Alternatively there may be used immobilized enzymes prepared according to the general method from said enzyme, said crude enzyme, or a product containing the enzyme.

As the substrate, there may be used dimethyl allyl diphosphates or geranyl diphosphates and isopentenyl diphosphates. As the reaction medium, water or an aqueous buffer solution, for example Tris buffer or phosphate buffer and the like, may be used.

By using the method of producing the mutant prenyl diphosphate synthase obtained by the present invention, the mutant prenyl diphosphate synthase derived from a archaea may be created that is more stable and thus easier to handle and that produces prrenyl diphosphate. Furthermore, there is also expected a creation of the farnesyl diphosphate-producing mutant prenyl diphosphate synthase that has the property of the prenyl diphosphate synthase prior to mutation (for example, salt stability or stability in a wide range of pH) added thereto.

In the claims and the specification of the present invention, amino acid residues are expressed by the one-letter codes or three-letter codes as described hereinbelow:

A; Ala; alanine
C; Cys; cysteine
D; Asp; aspartic acid
E; Glu; glutamic acid
F; Phe; phenylalanine
G; Gly; glycine
H; His; histidine
I; Ile; isoleucine
K; Lys; lysine
L; Leu; leucine
M; Met; methionine
N; Asn; asparagine
P; Pro; proline
Q; Gln; glutamine
R; Arg; arginine
S; Ser; serine
T; Thr; threonine
V; Val; valine
W; Trp; tryptophan
Y; Tyr; tyrosine Substitution of amino acid is expressed in the order of "the amino acid residue before substitution," "number of the amino acid residue," and "the amino acid residue after substitution," by the one-letter codes of amino acids. For example, the mutation in which a tyrosine residue at position 81 is replaced with a methionine residue is expressed as Y81M. Furthermore, the insertion of amino acid residues is expressed by "the number of the amino acid residue at the N-terminal side of the insertion site prior to insertion," "the amino acid residue that was inserted," and "the number of the amino acid residue at the C-terminal side of the insertion site prior to insertion." For example, the insertion of alanine in between the amino acid at position 84 and the amino acid at position 85 is expressed as 84A85.

EXAMPLES

The present invention is now explained with reference to specific examples, but they must not be construed to limit the invention in any way.

Example 1

Construction of a Plasmid Containing the Gene for Geranylaeranyl Diphosphate Synthase The gene for the geranylgeranyl diphosphate synthase (hereinafter referred to as SacGGPS) derived from *Sulfolobus acidocaldarius* was subcloned at the HindIII site of the plasmid vector pBluescript II (KS+) commercially available from Toyoboseki. The plasmid DNA was designated as pBs-SacGGPS. The SacGGPS gene is available from *Escherichia coli* DH5α (pGGPS1) that was internationally deposited on Jan. 31, 1994 with the National Institute of Bioscience and Human Technology Agency of Industrial Science and Technology, of Ibalaki, Japan under the accession number of FERM BP-4982.

Also, the entire nucleotide sequence of the SacGGPS gene has been published in Japanese Unexamined Patent Publication No. 7-308193 Shin-ichi Ohnuma et al. (1994) The Journal of Biological Chemistry Vol. 269:14792–14797, or in the genetic information data bank such as GenBank under the accession number D28748. Since *Sulfolobus acidocaldarius* is also available from various depositories of microorganisms such as ATCC etc. (as ATCC No. 33909), the DNA of the gene region of SacGGPS can be obtained by the conventional gene cloning method.

Example 2

Synthesis of the Oligonucleotides for Introducing Mutation

For introducing mutation of the gene of geranylgeranyl diphosphate synthase, the following oligonucleotides were designed and synthesized:

Primer DNA (T78F, H81A):
5'-CATACTTTTTTCCTTGTGGCTGATGATATCATG GATC-3' (SEQ ID No: 3)

Primer DNA (T78F, H81L):
5'-CATACTTTTTTCCTTGTGCTTGATGATATCATG GATC-3' (SEQ ID No: 4)

Primer DNA (F77Y, T78F, H81L):
5'-CATACTTATTTCCTTGTGCTTGATGATATCAT GGATC-3' (SEQ ID No: 5)

Primer DNA (F77Y, T78F, H81A):
5'-CATACTTATTTCCTTGTGGCTGATGATATCAT GGATC-3' (SEQ ID No: 6)

Primer DNA (F77Y, T78S, V80I, I84L, 84PS85):
5'-GTTCTTCATACTTATTCGCTTATTCATGATAGT ATT-3' (SEQ ID No: 7), and 5'-ATTCATGATGATC TTCCATCGATGGATCAAGAT-3' (SEQ ID No: 8).

Introduction of the mutation (F77Y, T78S, V80I, I84L, 84PS85) was effected using two nucleotides. First, mutation was introduced as mentioned in Example 3 using the oligonucleotide
5'-GTTCTTCATACTTATTCGCTTATTCATGATAG TATT-31 (SEQ ID No: 7) and a transformant was prepared in accordance with Example 4, and furthermore mutation was introduced into the plasmid thus obtained using the oligonucleotide
5'-ATTCATGATGATCTTCCATCGATGGATCAAGAT-3' (SEQ ID No: 8).

These nucleotides have a mutation in the codon encoding at least one amino acid residue selected from phenylalanine at position 77, threonine at position 78, valine at position 80, histidine at position 81, and isoleucine at position 84 in SacGGPS. In addition to the introduction of the codon encoding an amino acid that has been inserted in between isoleucine at position 84 and methionine at position 85, they are designed to newly introduce the cleavage site of the restriction enzyme BspHI (5'TGATGA3'), the cleavage site of the restriction enzyme EcoRV (5'GATATC3'), or the cleavage site of the restriction enzyme ClaI (5'ATCGAT3'). In the introduction of the cleavage site of BspHI, the amino acid sequence encoded by the SacGGPS gene does not change due to degeneracy of codons, or it is a site for an introduction of mutation. This is used to detect the substitution-mutated plasmid by means of agarose gel electrophoresis after digestion with an appropriate restriction enzyme, since the introduction of mutation by substitution into the SacGGPS gene simultaneously produces new cleavage sites of restriction enzymes.

These primer DNA's were subjected to phosphorylation treatment at 37° C. for 30 minutes in the reaction medium shown below followed by denaturation at 70° C. for 10 minutes:

10 pmol/µl primer DNA 2 µl

10×kination buffer 1 µl 10 mM ATP 1 µl

H2O 5 µl

T4 polynucleotide kinase 1 µl
wherein the 10×kination buffer is 1000 mM Tris-Cl (pH 8.0), 100 mM MgCl$_2$, and 70 mM DTT.

Example 3

The Introduction of Substitution-Mutation of the SacGGPSS Gene

Using each primer DNA constructed in Example 2, substitution-mutation was introduced into the plasmid prepared in Example 1 in accordance with the Kunkel method. Mutan-K kit commercially available from Takara Shuzo was used to perform the Kunkel method. The experimental procedure was as described in the kit insert. The substitution-mutation of the plasmid need not be conducted by the Kunkel method. For example, an identical result can be obtained by a method using the polymerase chain reaction (PCR).

Using *Escherichia coli* CJ236 in the Mutan-K kit as the host cell, a single strand DNA was obtained in which a thymine base in plasmid pBS-SacGGPS was replaced with a deoxyuracil base.

The single strand DNA thus obtained was used as the template in the reaction in which a primer DNA for synthesizing a complementary strand was treated in the following reaction solution at 65° C. for 15 minutes and then annealed by allowing to stand at 37° C. for 15 minutes:

Single strand DNA 0.6 pmol

Annealing buffer solution 1 µl

Primer DNA solution (Example 2) 1 µl

H2O make to a final volume of 10 µl
in which the annealing buffer solution is 200 mM Tris-Cl (pH 8.0), 100 mM MgCl$_2$, 500 MM NaCl, and 10 mM DTT.

Furthermore, 25 µl of the elongation buffer solution, 60 units of *Escherichia coli* DNA ligase, and 1 unit of T4 DNA polymerase were added to synthesize the complementary strands at 25° C. for 2 hours. The elongation buffer solution is 50 mM Tris-Cl (pH 8.0), 60 mM ammonium acetate, 5 mM MgCl$_2$, 5 mM DTT, 1 mM NAD, and 0.5 mM dNTP.

After the reaction is over, 3 µl of 0.2 M EDTA (pH 8.0) was added thereto and was subjected to treatment at 65° C. for 5 minutes to stop the reaction.

Example 4

Construction of a Recombinant Having a Gene in Which Substitution-Mutation Has Been Introduced into the SacGGPS Gene The DNA solution constructed in accordance with Example 3 was used to transform *Escherichia coli* XL1-Blue by the CaCl$_2$ method. An alternative method such as electroporation gives a similar result. A host cell other than *Escherichia coli* XL1-Blue, for example JM109 and the like also gave a similar result.

The transformant obtained by the CaCl$_2$ method was plated onto the agar plate containing ampicillin, a selectable marker of transformants, and was incubated overnight at 37° C.

Of the transformants obtained as above, the substitution-mutated pBs-SacGGPS plasmid that has a cleavage site of BspHI, EcoRV or ClaI was selected. The nucleotide sequence in the neighborhood of the codon corresponding to the amino acid residue that undergoes mutation of the SacGGPS gene of the selected substitution-mutated pBs-SacGGPS plasmid was determined by the dideoxy method. As a result, the pBs-SacGGPS plasmid containing the following five mutated SacGGPS genes was obtained. The nucleotide sequences encoding the amino acid sequences from the amino acid at position 77 to the amino acid at position 85 is shown below:

Mutation Nucleotide sequence

T77F, H81A: 5'-TTTTTCCTTGTGGCTGATGA TATCATG-3' (SEQ ID No: 9)

T78P, H81L: 5'-TTTTTCCTTGTGCTTGATG ATATCATG-3' (SEQ ID No: 10)

F77Y, T78F, H81L: 5'-TATTTCCTTGTGCTTGATG ATATCATG-31 (SEQ ID No: 11)

F77Y, T78F, H81A: 5'-TATTTCCTTGTGGCTGATGA TATCATG-3' (SEQ ID No: 12)

F77Y, T78S, V80I, I84L, 84PS85: 5'-TATTCG CTTATTCATGATGATCTTCCATCGATG-3' (SEQ ID No: 13)

Wild type: 5'-TTTACGCTTGTGCATGATGATATTATG-3' (SEQ ID No: 14).

Example 5

Measurement of Activity of the Mutant Prenyl Diphosphate Synthase

Crude enzyme solutions were prepared as follows from 6 transformants comprising 5 mutant SacGGPS genes and one wild type SacGGPS gene obtained in Example 4.

Figure 2:
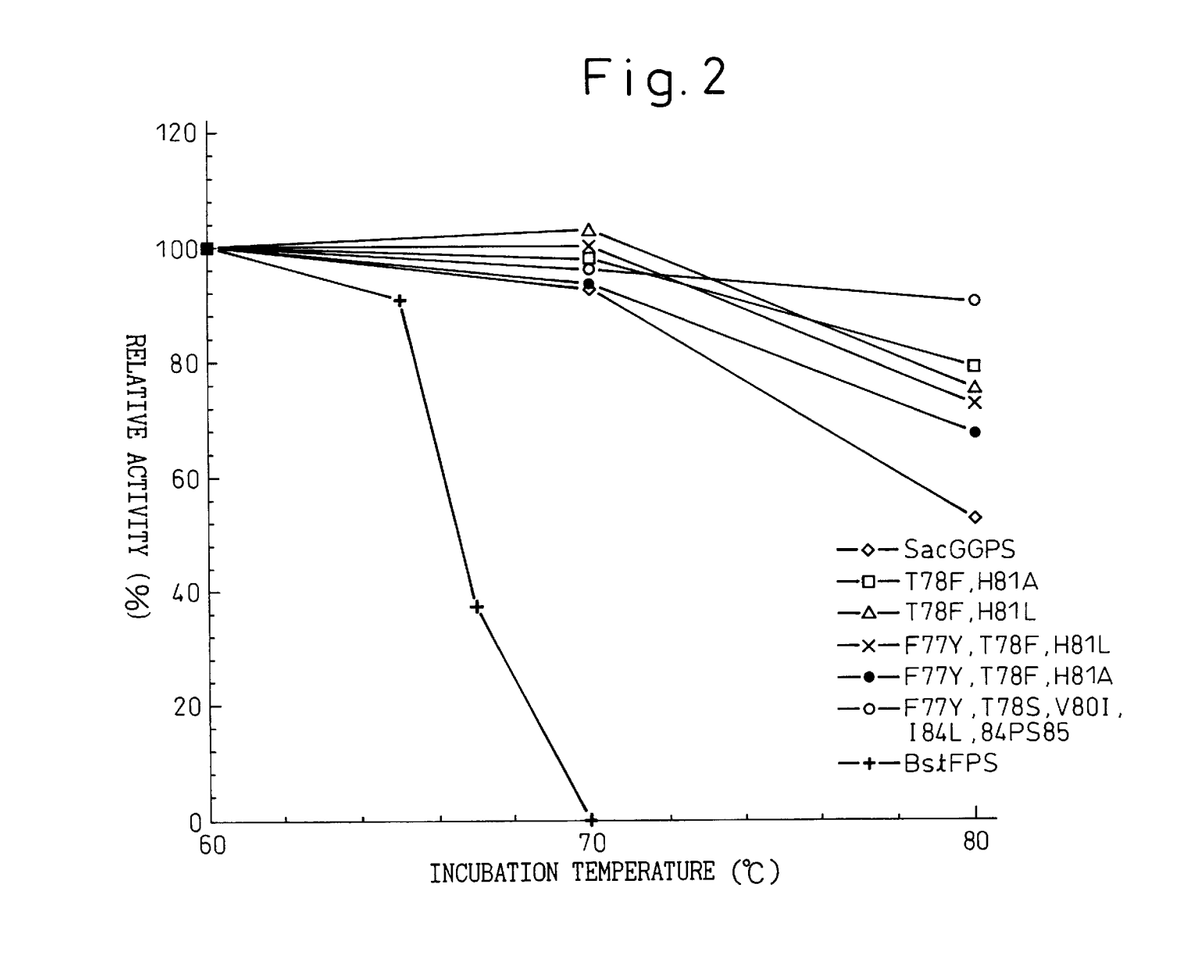
FIG. 2 is a graph showing the thermal stability of the mutant prenyl diphosphate synthase. The ordinate shows the relative activity to 100% at incubation at 60° C. The abscissa shows the incubation temperature. SacGGPS is the geranylgeranyl diphosphate synthase prior to mutation. The others represent the mutant type enzyme of each. BstFPS is the farnesyl diphosphate synthase derived from *Bacillus stearothermophillus*.

The transformant cultured overnight in the 2×LB medium was centrifuged to harvest cells, and then the cells were suspended into a buffer for cell homogenization (50 mM calcium phosphate buffer solution (pH 5.8), 10 mM β-mercaptoethanol, 1 mM EDTA). This was homogenized by sonnication and then centrifuged at 4° C. at 10,000 r.p.m. for 10 minutes. The supernatant obtained was treated at 55° C. for 12 hours to inactivate the activity of prenyl diphosphate synthase derived from *Escherichia coli*. This was further centrifuged under the same condition and the supernatant obtained was used as a crude enzyme extract. When thermo stability was investigated the enzyme extract was incubated at 60° C., 70° C., or 80° C. (60° C., 65° C., 67° C., or 70° C. for the enzymes derived from *Bacillus stearothermophilus*) for one hour prior to reaction. The reaction was conducted at 55° C. for 15 minutes in the following reaction solution:

[1-$^{14}$C]-isopentenyl diphosphate (1 Ci/mol) 25 nmol
Allylic diphosphate (geranyl diphosphate) 25 nmol
Potassium phosphate buffer (pH 5.8) 10 mM
$MgCl_2$ 5 mM
Enzyme solution 100 μg
$H_2O$ to make 200 μl After the reaction is over, 200 μl of saturated NaCl was added to the reaction solution and 1 ml of water-saturated butanol was added thereto, which was then agitated, centrifuged, and separated into two phases. To 800 μl of the butanol layer obtained was added 3 ml of a liquid scintillator and then the radioactivity was measured by the scintillation counter. The result is shown in FIG. 2.

The mutant prenyl diphosphate synthase has exhibited a thermo stability which is equal to that of the native geranylgeranyl diphosphate synthase, and is higher than that of the farnesyl diphosphate synthase derived from *Bacillus stearothermophilus*.

The solvent is evaporated from the remainder of the butanol layer by purging nitrogen gas thereinto while heating the layer in order to concentrate to a volume of about 0.5 ml. To the concentrate were added 2 ml of methanol and one ml of potato acid phosphatase solution (2 mg/ml potato acid phosphatase, 0.5 M sodium acetate (pH 4.7)) to effect the dephosphorylation reaction at 37° C. Subsequently the dephosphorylated reaction product was extracted with 3 ml of n-pentane.

Figure 3:
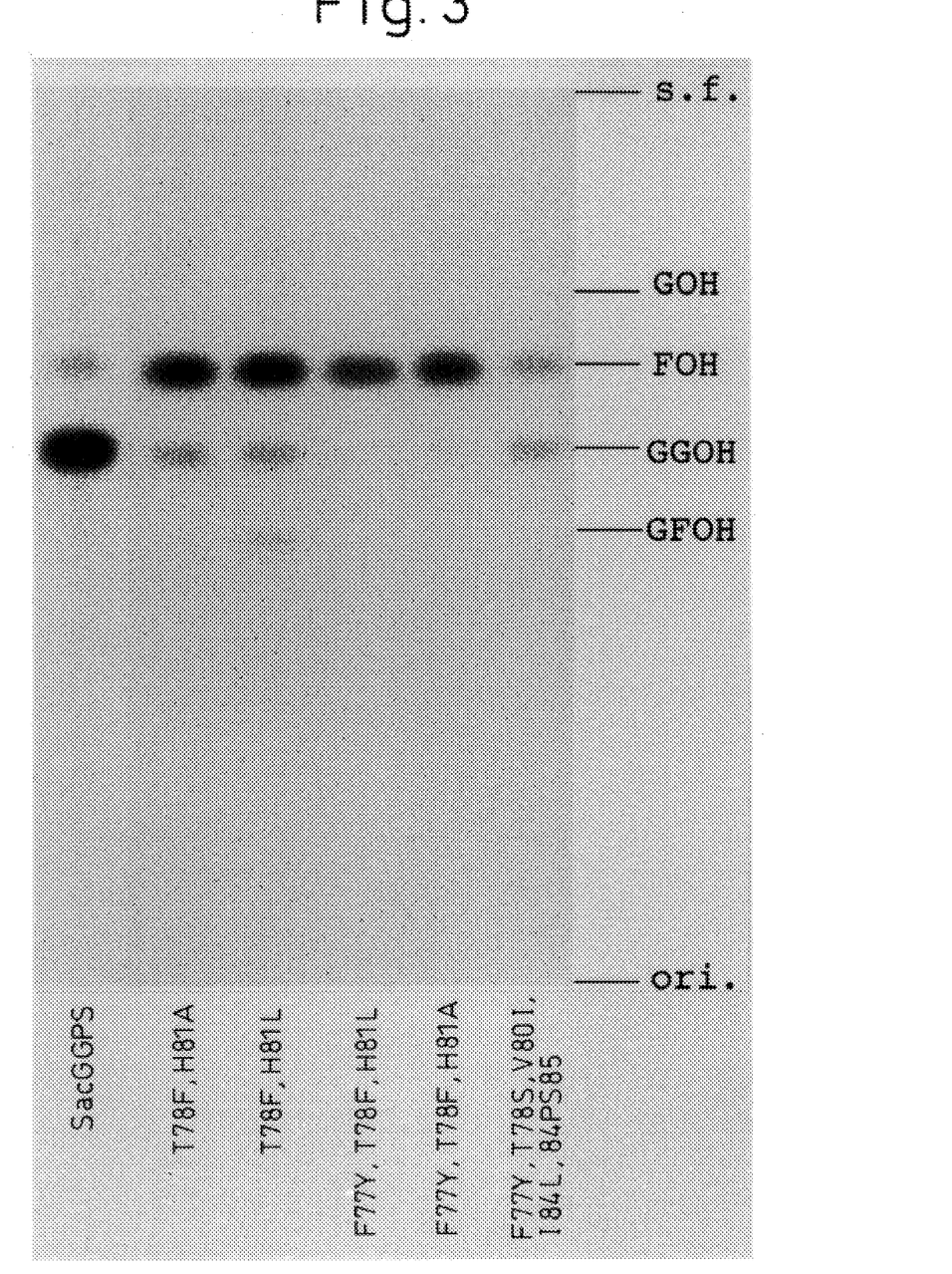
FIG. 3 shows a photograph of a development pattern of thin layer chromatography of the dephosphorylated reaction products of the mutant prenyl diphosphate synthase when geranyl diphosphate was used as the allylic substrate. In the figure, ori. represents the origin of development, and s.f. represents the solvent front.

This was concentrated by evaporating the solvent by purging nitrogen gas thereinto, which was then analyzed by TLC (reverse phase TLC plate: LKC18 (Whatman), development solvent: acetone/water=9/1). The developed dephosphorylated reaction product was analyzed by the Bio Image Analyzer BAS2000 (Fuji Photo Film) to determine the location of radioactivity. The result when geranyl diphosphate was used as the allylic substrate is shown in FIG. 3.

The reaction product of the mutant prenyl diphosphate synthase was shown to be a farnesyl diphosphate.

We claim:

1. A mutant prenyl diphosphate synthase having a modified amino acid sequence, wherein said mutant prenyl diphosphate synthase comprises an aspartic acid-rich domain having the sequence, $D_1D_2X_1X_2(X_3X_4)D_3$, in region II of said mutant prenyl diphosphate synthase, wherein each of $D_1$, $D_2$ and $D_3$ denote an aspartic acid residue; $X_1$, $X_2$, $X_3$ and $X_4$ are each independently any amino acid and $X_3$ and $X_4$ are each optionally independently present in the aspartic acid rich domain, and wherein said mutant prenyl diphosphate synthase comprises (1) at least one amino acid substitution, said at least one amino acid substitution located at at least one amino acid position selected from (a) an amino acid between $D_1$ and the amino acid residue at the fifth position upstream of $D_1$ and (b) the amino acid residue located one amino acid position upstream of $D_3$; (2) at least one additional amino acid inserted between $D_3$ and the first amino acid upstream of $D_3$; or a combination of (2) and (3);

wherein said mutant prenyl diphosphate synthase synthesizes prenyl diphosphate which is shorter than prenyl diphosphate synthesized by a corresponding wild-type enzyme.

2. A mutant prenyl diphosphate synthase according to claim 1 wherein said mutant has the enzymatic activities and thermo stability of wild type prenyl diphosphate synthase.

3. A mutant enzyme according to claim 1 wherein the reaction product of the prenyl diphosphate synthase is farnesyl diphosphate.

4. A mutant enzyme according to claim 1 wherein the prenyl diphosphate synthase is of the homodimer-type.

5. A mutant enzyme according to claim 1 wherein the prenyl diphosphate synthase is derived from archaea.

6. A mutant enzyme according to claim 1 wherein the prenyl diphosphate synthase is derived from *Sulfolobus acidocaldarius*.

7. A mutant enzyme according to claim 1 wherein the prenyl diphosphate synthase is a thermostable enzyme.

8. A mutant prenyl diphosphate synthase according to claim 1, wherein at least one amino acid selected from phenylalanine at position 77, threonine at position 78, valine at position 80, histidine at position 81, and isoleucine at position 84 has been substituted by another amino acid, or one or more amino acids have been inserted in between isoleucine at position 84 and methionine at position 85 in the geranylgeranyl diphosphate synthase as set forth in SEQ ID No: 1.

9. A mutant prenyl diphosphate synthase according to claim 1 wherein at least one amino acid selected from phenylalanine at position 77, threonine at position 78, valine at position 80, histidine at position 81, and isoleucine at position 84 has been substituted by another amino acid, and/or two amino acids have been inserted in between isoleucine at position 84 and methionine at position 85 in the geranylgeranyl diphosphate synthase as set forth in SEQ ID NO: 1, wherein the phenyl alanine at position 77 has been replaced with tyrosine, the threonine at position 78 has been replaced with phenylalanine or serine, the valine at position 80 has been replaced with isoleucine, the histidine at position 81 has been replaced with leucine or alanine, or the isoleucine at position 84 has been replaced with leucine; or proline and serine have been inserted in between the isoleucine at position 84 and the methionine at position 85.

10. A mutant prenyl diphosphate synthase according to claim 1, wherein the mutant prenyl diphosphate synthase is derived from a native geranylgeranyl diphosphate synthase of an organism selected from the group consisting of *Arabidopsis thaliana, Lupinas albus, Capsicum annuum, Sulfolobus acidocaldarius, Rhodobactor sphaeroides, Rhodobactor capsulatus, Erwinia herbicola, Myxococcus thaliana* and *Neurospora crassa*.

11. A DNA encoding an enzyme according to claim 1.

12. An RNA transcribed from a DNA according to claim 11.

13. A recombinant vector comprising a DNA according to claim 11.

14. A host organism transformed with a recombinant vector according to claim 13.

15. A process for producing a mutant enzyme according to claim 1, said method comprising the steps of culturing a host transformed with an expression vector comprising a DNA coding for the mutant enzyme and of harvesting the expression product from the culture.

16. A process for producing a prenyl diphosphate having not more than 15 carbons comprising the step of bringing an enzyme according to claim 1 or any of claims 2 to 10 or an enzyme produced by the method according to claim 15 into contact with a substrate selected from the group consisting of isopentenyl diphosphate, dimethylallyl diphosphate, and geranyl diphosphate.

* * * * *